United States Patent [19]

Cassou et al.

[11] 4,432,753

[45] Feb. 21, 1984

[54] APPARATUS FOR ARTIFICIAL INSEMINATION

[76] Inventors: Bertrand Cassou, Saint Symphorien des Bruyeres; Maurice Cassou; Robert Cassou, both of Rue Clemenceau, all of 61300 L'Aigle, France

[21] Appl. No.: 386,355

[22] Filed: Jun. 8, 1982

[30] Foreign Application Priority Data

Dec. 3, 1981 [FR] France .............................. 81 22628

[51] Int. Cl.³ .............................................. A61M 1/00

[52] U.S. Cl. ...................................................... 604/55

[58] Field of Search ...................... 604/54, 55, 49, 218, 604/220, 60, 61, 38, 135, 183

[56] References Cited

U.S. PATENT DOCUMENTS

| | | | |
|---|---|---|---|
| 2,503,341 | 4/1950 | Kissileff | 604/220 |
| 2,751,907 | 6/1956 | Hickey | 604/60 |
| 4,223,674 | 9/1980 | Fluent et al. | 604/61 |

*Primary Examiner*—John D. Yasko

*Attorney, Agent, or Firm*—Fidelman, Wolffe & Waldron

[57] ABSTRACT

The invention discloses a multi-shot artificial insemination device and interchangeable and disposable reservoir tubes connectable thereto such that plural doses of liquid semen are sequentially discharged from one end of a tube by step-wise displacement of a plunger into another end of the tube. The apparatus is configured for easy, secure connection and support of a rear end of a reservoir tube to the device while a freely protruding front end of the reservoir is of sufficient length and shape for insertion into an animals cloaca for insemination thereof upon actuation of the device.

10 Claims, 2 Drawing Figures

APPARATUS FOR ARTIFICIAL INSEMINATION

The present invention relates to apparatus for artificial insemination of small animals and particularly, but not exclusively, poultry such as hens, and especially multi-shot apparatus comprising a holder with a cylindrical passage for accommodating means for ejecting the semen and a reservoir tube containing semen (a so-called "paillette") which is secured against the passage at the front of the holder.

When the semen ejection means are formed by a piston rod sliding in the passage, and provided with a step wise displacement mechanism, such multi-shot apparatus enables several insemination operations to be performed using a pre-determined fraction or dose of the total volume of semen (or other product to be injected) contained in a given reservoir tube which enables several animals to be inseminated in quick succession.

Apparatus of this kind is known, for example in French Pat. No. 79 02020, which is designed for inseminating guinea fowl. In that apparatus, however, the guide passage is formed in a projection from the holder, the inner diameter of the reservoir tube being almost equal to the outer diameter of the piston rod, and the reservoir tube engages the holder only by its rear edge engaging the front face of this projection. The tube is secured by a flexible protective sleeve which surrounds the assembly comprising the reservoir tube and the projection and is fixed at its rear end to the projection, either by a clamp ring engaging a converging outer surface of the projection or by its own elasticity on a rib, for example a spiral, on the projection, while the front end of the sleeve presents a converging or rounded edge acting as abutment for the front of the reservoir tube within it. The converging or round edge facilitates penetration into the cloaca and reduces risk of injury to the cloaca wall. Moreover the reduced size of the orifice defined by the converging or rounded end of the sleeve gives a nozzle effect and enables the semen to be ejected as a jet under the pressure produced by the mechanical force supplied by the piston rod, without forming a drop "beading" on the end of the sleeve and which, staying fixed to the sleeve by capillarity would be unused in the insemination, thus causing an error in the dose actually injected and also increased cost of the operation, bearing in mind the high cost of semen.

For insemination of guinea fowl, a reservoir tube of this kind has a capacity of about 0.5 $cm^3$ which enables 20 to 25 animals to be inseminated given the usual concentration of semen in the tube. For other species, for example of the gallus genus such as hens, the concentration must be different and the capacity of 0.5 $cm^3$ only gives about 10 shots, which would need the reservoir tube to be changed too often with consequent waste of time. Moreover the cost of the reservoir tube increases the cost per injected dose. Lastly, the sleeve, generally made from polyvinyl chloride, like the reservoir tube, is also of relatively high cost and burdens the cost of use.

The object of the present invention is to avoid or reduce some or all of the above disadvantages, and especially to reduce the cost of the removable and replaceable part previously formed by the reservoir tube and sleeve.

The present invention provides artificial insemination apparatus comprising a body member presenting a push rod passage, ejection means associated with said passage, a reservoir tube for containing semen and presenting a converging front end for self-supporting insertion into an animal and a rear end, said body member presenting a snout solid therewith and through which said passage extends, said snout being shaped for said rear end of said tube to be force fitted directly thereon, whereby said ejection means may be actuated to eject semen from said front end of said tube into the animal.

Accordingly, it is no longer necessary to provide a sleeve additional to the reservoir tube to secure it to the body member and facilitate penetration without injury to the animal.

In a particularly advantageous embodiment of the invention, the internal diameter of said tube is substantially greater than the inner diameter of said passage.

This enables significantly increased capacity reservoir tubes to be used, which may, for example, contain 20 to 25 doses of the gallus species with a capacity of about 1.2 $cm^3$.

Preferably said snout presents externally in succession along said push-rod passage an engagement surface for fitting in said rear end of said tube and a free cylindrical surface of outer diameter less than the inner diameter of said tube. The free engagement surface can penetrate into the reservoir tube and engage a piston bung in the tube, cooperating with a piston rod in said passage.

Advantageously and including a ring presenting an inner surface for clamping said rear end of said tube onto said snout. In this case, preferably said ring presents an elongate free end portion for surrounding and supporting said tube, said free end portion having an inner diameter slightly larger than the outer diameter of said tube. The free end portion acts to guide and support the reservoir tube over part of its length, giving it additional rigidity to its own self-supporting rigidity, and partly replacing the reinforcement of the sleeve of the prior apparatus.

Other features and advantages of the invention will appear from the following description, given by way of nonlimitative example with reference to the accompanying drawings, in which.

Figures 1, 2:
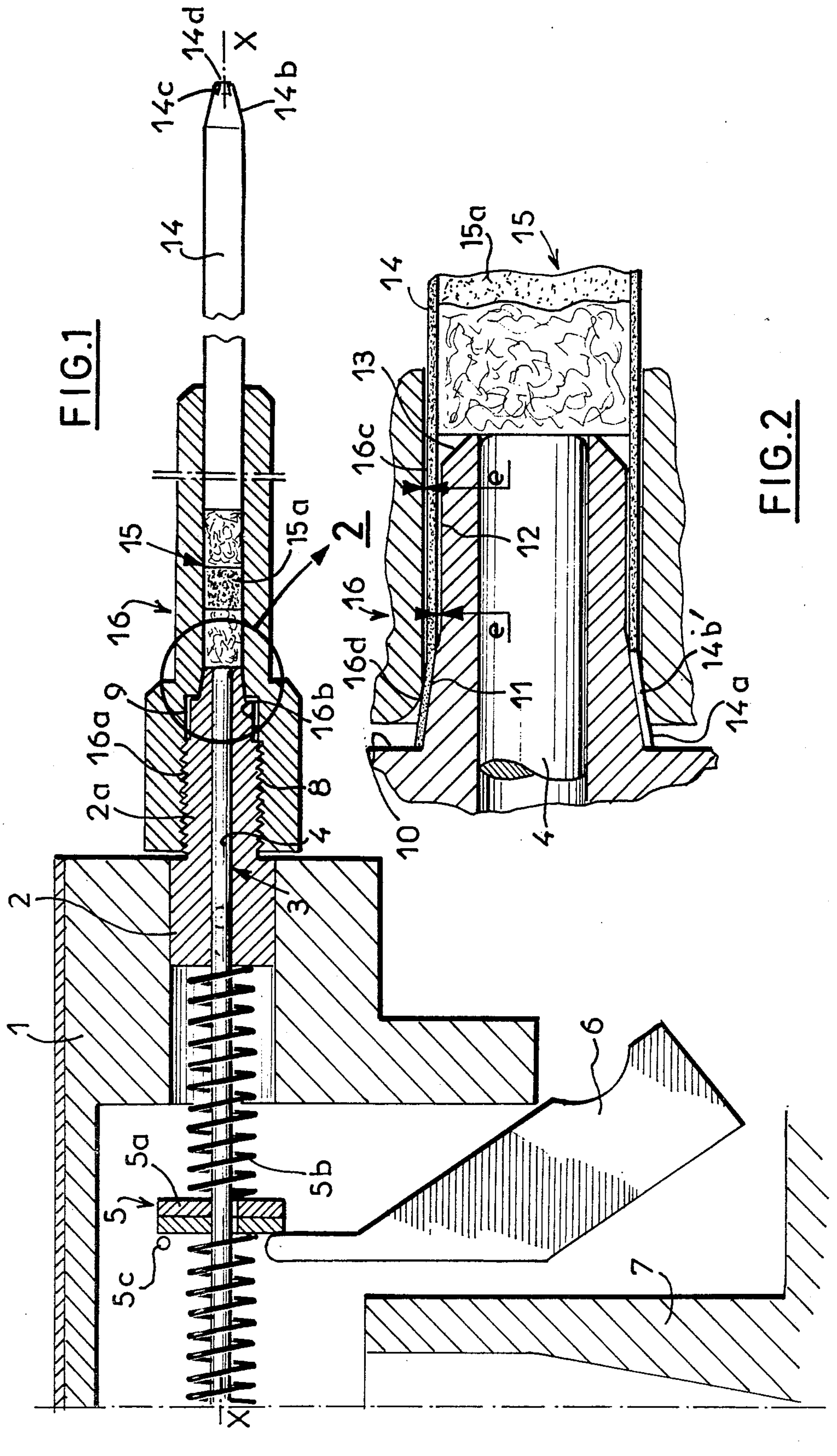
FIG. 1 is a partial sectional view of apparatus according to an embodiment of the invention.
FIG. 2 is an enlarged detail view of a gripping zone for a reservoir tube on a holder in the apparatus of FIG. 1.

The apparatus shown in the drawings comprises a pistol-type holder 1 presenting a front face 1*a* in which is fixed a block 2 presenting a barrel portion 2*a* projecting from the face 1*a* in a direction X—X. The block 2 and projecting barrel 2*a* present a cylindrical guide passage 3 extending in the direction X—X within which is mounted slidingly a piston-rod 4 which extends behind the block 2 within the holder 1 and is provided with step-wise displacement means 5, including drilled plates 5*a*, springs 5*b* and abutments 5*c* which will not be described here in more detail, a description being available in French Pat. No. 7902020. The step-wise displacement means 5 are actuated by a trigger 6 which projects from a butt 7 of the holder extending transversely to the axis X—X.

The projecting barrel 2*a* of the block 2 comprises at its outer end in succession from the face 1*a* of the holder in the direction X—X a cylindrical surface presenting a fixing thread 8, a cylindrical bearing surface 9 of slightly smaller diameter, a radial shoulder 10, a converging truncated coneshape surface 11 of small angle and lastly a cylindrical part 12 terminating in a chamfered end 13.

The pistol is associated with a reservoir tube or "paillette" 14 made, for example, of polyvinyl chloride, containing animal semen, whose rear end is closed by a piston-bung 15. The inner diameter of the paillette is slightly greater than the diameter of the cylindrical bearing surface 12 of the barrel 2a, with a clearance e therebetween. Its extreme rear end 14a is force fitted onto the conic surface 11 of the barrel, the stretching of its normally cylindrical end giving firm engagement with the barrel. This fitting ensures that the barrel 2a penetrates into the reservoir tube 14 and its end 13 acts as abutment for the piston-bung 15.

There can also advantageously be provided a longitudinal slot 14b' in the extreme rear end 14a of the tube, the slot being provided to facilitate the force-fit of the paillette onto the barrel 2a of the pistol, and also to facilitate its ejection once it is emptied.

Moreover, the piston-bung 15 comprises three parts juxtaposed axially, the middle part being coloured so that when the bung almost reaches the front end of the paillette 14b, the coloured part acts as a visual warning for the inseminator that the semen in the paillette is almost finished, with only two or three more shots to go. The bung also enables rapid and easy suction of the liquid into the paillette when it is filled, before use, from a bottle containing the liquid (such as collected cock's semen for example or other liquid to be injected). To fill the paillette, its end opposite to the end 14a is introduced through the neck of the bottle into the liquid to be filled into the paillette, and using the mouth or a tube connected to a bulb, the liquid is readily sucked up without requiring special and complicated apparatus. In addition, the central part of the bung is made from a special powder which gelifies immediately when it contacts the liquid entering the paillette to give a seal at the end of the tube, where the bung is positioned after filling.

The apparatus is completed by a clamping ring 16 which comprises successively from rear to front a connector part 16a with an internal thread which screws onto the thread 8 of the barrel, a chamber 16b which leaves a clearance round the bearing surface 9 and shoulder 10 of the barrel, and an extreme end comprising a cylindrical bore of inner diameter, slightly larger than the diameter of the reservoir tube 14, so as to leave a clearance e, the rear edge of this bore presenting a radius or bead 16d which presses the stretched end 14a of the reservoir tube onto the conic surface 11 of the barrel. This radius 16d is polished, and avoids the reservoir tube 14 being cut at the engagement point which would enable the tube to escape from the pistol when the piston rod 4 is actuated. The front cylindrical part 16c extends for a certain length around the reservoir tube 14 so as to reinforce the positioning and the rigidity of the tube, the length being as much as a third, a half, or even more of the length of the tube 14.

At its front end, the reservoir tube 14 presents a converging truncated cone portion 14b, which ends in a lip 14c turned inwards to form a rim or hem, and which may even extend back inwards axially of the tube, the lip defining an ejection orifice 14d.

We claim:

1. A multi-shot artificial insemination apparatus comprising:
   - a body presenting a snout and a passage through said snout;
   - a disposable reservoir means for containing plural doses of liquid semen and comprising a tube having a rear end;
   - said snout and said tube rear end being cooperatively configured to fit said rear end to said snout in alignment with said passage;
   - said tube further comprising a blunt convergent front end and a length from said rear end to said front end and freely protruding sufficiently far from said snout for insertion of said tube into an animals cloaca to facilitate said insemination;
   - a plunger extensible through said passage and into said tube rear end; and
   - means for displacing said plunger stepwise to discharge successive doses of said liquid semen from said tube through said front end to said cloaca.
2. Apparatus as in claim 1 wherein an internal diameter of said tube is substantially greater than a diameter of said passage.
3. Apparatus as in claim 2 wherein said snout comprises, externally in succession along said passage, an engagement surface means for fitting in said rear end of said tube and a free cylindrical surface of outer diameter less than the internal diameter of said tube.
4. Apparatus as in claim 1 and including a ring comprising an inner surface means for clamping said rear end of said tube onto said snout.
5. Apparatus as in claim 4 wherein said snout further comprises an externally threaded portion and said ring further comprises an internally threaded portion so that said ring may be secured to said body member by screwing said threaded portions together.
6. Apparatus as in claim 4 wherein said ring further comprises an elongate free end portion surrounding and supporting said rear end of said tube, said free end portion having an inner diameter slightly larger than an outer diameter of said tube.
7. Apparatus as in claim 4 wherein said inner surface means of said ring comprises a rounded read edge such that cutting of said rear end by said clamping is avoided.
8. Apparatus as in claim 4 wherein the rear end of said tube comprises a longitudinal slit such that fitting of said rear end onto said engagement surface means of said snout is facilitated.
9. Apparatus as in claim 1 wherein said front end of said tube has a convergent truncated cone shape with an inwardly turned lip.
10. Apparatus as in claim 1 wherein said passage and said snout are formed in a block member which is secured in a front portion of said body.

* * * * *